United States Patent [19]
Little et al.

[11] Patent Number: 6,027,709
[45] Date of Patent: Feb. 22, 2000

[54] FLUORESCENT CYANINE DYES

[75] Inventors: Garrick Murray Little; Ramesh Raghavachari; Narasimhachari Narayanan; Harry Leonard Osterman, all of Lincoln, Nebr.

[73] Assignee: Li-Cor Inc., Lincoln, Nev.

[21] Appl. No.: 08/781,326

[22] Filed: Jan. 10, 1997

[51] Int. Cl.[7] .................... A61K 51/00; A61M 36/14
[52] U.S. Cl. .............. 424/1.65; 536/26.1; 536/18.7; 536/22.1; 424/1.37; 424/9.6
[58] Field of Search .................... 536/1.11, 18.7, 536/22.1, 26.1, 26.12, 26.8; 548/400; 540/1; 424/1.37, 1.65, 9.6, 9.7, 9.8

[56] References Cited

U.S. PATENT DOCUMENTS

| | | | |
|---|---|---|---|
| 4,711,955 | 12/1987 | Ward et al. | 536/29 |
| 5,047,519 | 9/1991 | Hobbs, Jr. et al. | 536/23 |
| 5,091,519 | 2/1992 | Cruickshank | 536/29 |
| 5,151,507 | 9/1992 | Hobbs, Jr. et al. | 536/23 |
| 5,241,060 | 8/1993 | Engelhardt et al. | 536/27 |
| 5,268,486 | 12/1993 | Waggoner et al. | 548/427 |
| 5,332,666 | 7/1994 | Prober et al. | 435/91.5 |
| 5,366,623 | 11/1994 | Middendorf . | |
| 5,436,134 | 7/1995 | Haugland et al. | 435/34 |
| 5,589,250 | 12/1996 | Asai et al. | 428/209 |
| 5,622,821 | 4/1997 | Selvin et al. | 435/6 |

FOREIGN PATENT DOCUMENTS

| | | |
|---|---|---|
| 0670374 | 9/1995 | European Pat. Off. . |
| 06222059 | 8/1994 | Japan . |
| 07083924 | 3/1995 | Japan . |
| 07083925 | 3/1995 | Japan . |
| 07145148 | 6/1995 | Japan . |
| 9504747 | 2/1995 | WIPO . |
| 9623525 | 8/1996 | WIPO . |

OTHER PUBLICATIONS

Mujumdar, et al., *Bioconjugate Chem.* 1993, 4, 105–11.
Narayanan, et al., *J. of Organic Chem.* 1995, 60, 2391–5.
Mujumdar, et al., Bioconjugate Chem. 1996, 7, 356–362.
Steffens et al., Genome Res. 1995, 393–99 and Erratum.
Oetting et al., Genomics, 1995, 30, 450–58.

*Primary Examiner*—Jose G. Dees
*Assistant Examiner*—Dameron Jones
*Attorney, Agent, or Firm*—Rothwell, Figg, Ernst & Kurz

[57] ABSTRACT

New fluorescent cyanine dyes are useful as reporter groups for labeling biomolecules.

17 Claims, No Drawings

FLUORESCENT CYANINE DYES

FIELD OF THE INVENTION

This invention relates to new and useful cyanine dyes. The dyes are useful as fluorescent labels of biomolecules, such as oligonucleotides and deoxyribonucleosides. The biomolecules can be labeled with the dyes either directly or indirectly through a phosphoramidite.

BACKGROUND OF THE INVENTION

DNA sequencing is an important analytical technique of molecular biology. The development of sequencing techniques has led to advances in both the analysis and manipulation of genetic material.

Well-known methods of DNA sequencing include the Maxam-Gilbert chemical degradation method, described in Maxam et al., *Meth. in Enzym.* 65:499 (1980), and the Sanger dideoxy chain termination technique, described in Sanger et al., *P.N.A.S. USA* 74:5463 (1977). In each method DNA fragments labeled with $^{32}P$ are generated which are analyzed by gel electrophoresis. Both methods are useful, although they can prove to be difficult and slow.

As a result, other methods have been sought, including those which do not rely upon short-lived radioisotopes, such as $^{32}P$. Several alternative methods of detection have been developed based on fluorescent labels. DNA fragments are labeled with one or more fluorescent dyes. Excitation with an appropriate light source (laser) causes a characteristic emission from the dye, thereby identifying the band. Even minute amounts of a biomolecule can be detected using such a method.

Among the fluorescent dyes which have been developed are a number of cyanine dyes which have been used to label various biomolecules for highly sensitive detection schemes. For example, U.S. Pat. No. 5,268,486, issued to Waggoner et al. (1993), discloses and claims fluorescent arylsulfonated cyanine dyes having large extinction coefficients and quantum yields for the purpose of detection and quantification of labeled components. Although the dyes described in this patent are useful, additional cyanine dyes are sought.

Recent advances in solid state laser technology have led to the commercial availability of inexpensive, reliable lasers with wavelengths near 680 nm. Suitable dyes excited with such lasers will fluoresce in the near infrared (NIR) region of the electromagnetic spectrum. These fluorescence signals will be free of background fluorescence from most biological systems. Unfortunately, there are few dyes available commercially which have suitable absorption/fluorescence properties and useful linking groups for attachment to biomolecules, and those that presently are available are quite expensive.

Accordingly, it is an object of the present invention to provide new cyanine dyes useful in labeling biomolecules.

SUMMARY OF THE INVENTION

Novel sulfonated cyanine compounds are useful for labeling various types of biomolecules. The compounds have the general formula

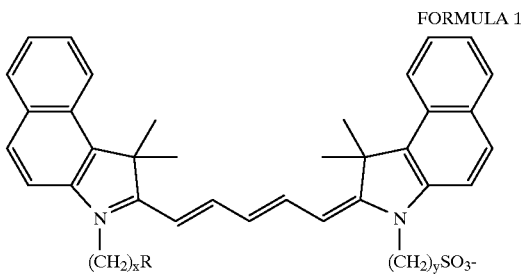

FORMULA 1 wherein R is —OH, —$CO_2H$, —$NH_2$ or —NCS; and each of x and y, independently, is an integer from 1 to about 10. In one preferred embodiment, R is —OH, x is 6 and y is 4. In a second preferred embodiment, R is —$CO_2H$, x is 5 and y is 4.

The compounds of this invention wherein R is —$CO_2H$ can be attached to a biomolecule through an amine group or a hydroxyl group on the latter. The compounds of this invention wherein R is —NCS can be attached to a biomolecule through an amine group on the latter. The compounds of this invention wherein R is —OH can be attached to a biomolecule indirectly through a phosphoramidite ultimately forming a phosphate linkage. In each embodiment the labeled biomolecule then can be excited with a solid state laser and detected with high sensitivity through the fluorescence of the label. The dyes of this invention have advantageous solubility and light absorbing/emitting properties.

DETAILED DESCRIPTION OF THE INVENTION

The compounds of this invention have the general formula

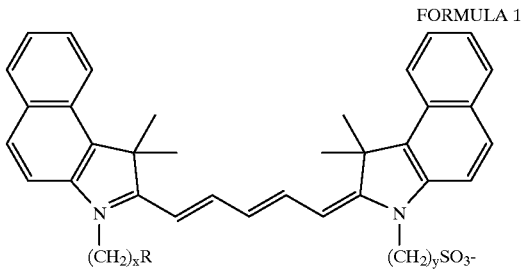

FORMULA 1 wherein R is —OH, —$CO_2H$, —$NH_2$, or —NCS and each of x and y, independently, is an integer selected from 1 to about 10. In preferred embodiments, each of x and y, independently, is an integer between about 2 and 6. In one most preferred embodiment, the dye is N-(6-hydroxyhexyl) N'-(4-sulfonatobutyl)-3,3,3',3'-tetramnethylbenz(e) indodicarbocyanine, which has the formula:

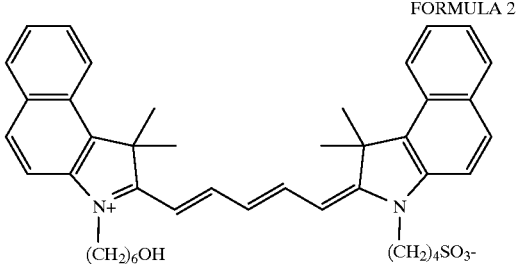

FORMULA 2

In a second most preferred embodiment, the dye is N-(5-carboxypentyl)N'-(4-sulfonatobutyl)3,3,3',3'-tetramethylbenz(e)indodicarbocyanine, which has the formula:

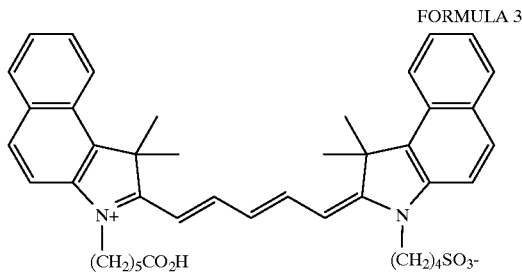

FORMULA 3

These two dyes are preferred because they have commercially available precursors for the linking groups: 6-bromohexanol, 6-bromohexanoic acid and 1,4-butane sultone (all available from Aldrich Chemical Co., Milwaukee, Wis.). The linking groups provide adequate distance between the dye and the biomolecule for efficient attachment without imparting excessive hydrophobicity. The resulting labeled biomolecules retain their solubility in water and are well-accepted by enzymes.

The dyes of this invention wherein R is —$CO_2H$ or —OH can be synthesized, as set forth in detail in the examples below, by reacting the appropriate N-(carboxyalkyl)- or N-(hydroxyalkyl)-1,1,2-trimethyl-1H-benz(e)indolinium halide, preferably bromide, with sulfonatobutyl-1,1,2-trimethyl-1H-benz(e)indole at a relative molar ratio of about 0.9:1 to about 1:0.9, preferably 1:1 in an organic solvent, such as pyridine, and heated to reflux, followed by the addition of 1,3,3-trimethoxypropene in a relative molar ratio of about 1:1 to about 3:1 to the reaction product and continued reflux. The mixture subsequently is cooled and poured into an organic solvent such as ether. The resulting solid or semi-solid can be purified by chromatography on a silica gel column using a series of methanol/chloroform solvents.

As an alternative, two-step, synthesis procedure, also detailed in the examples below, N-4-sulfonatobutyl-1,1,2-trimethyl-1H-benz(e)indole and malonaldehyde bis (phenylimine)-monohydrochloride in a 1:1 molar ratio can be dissolved in acetic anhydride and the mixture heated. The acetic anhydride is removed under high vacuum and the residue washed with an organic solvent such as ether. The residual solid obtained is dried and subsequently mixed with the appropriate N-(carboxyalkyl)- or N-(hydroxyalkyl)-1,1,2-trimethyl-1H-benz(e)indolinium halide in the presence of an organic solvent, such as pyridine. The reaction mixture is heated, then the solvent is removed under vacuum, leaving the crude desired dye compound. The procedure was adapted from the two step procedure set forth in Ernst, L. A., et al., *Cytometry* 10:3–10 (1989).

The dyes also can be prepared with an amine or isothiocyanate terminating group. For example, N-(ω-aminoalkyl)-1,1,2-trimethyl-1H-benz(e)indolenium bromide hydrobromide (synthesized as in N. Narayanan and G. Patonay, *J. Org. Chem.* 60:2391–5 (1995)) can be reacted to form dyes of formula 1 wherein R is —$NH_2$. Salts of these amino dyes can be converted to the corresponding isothiocyanates by treatment at room temperature with thiophosgene in an organic solvent such as chloroform and aqueous sodium carbonate.

The dye compounds of this invention have a maximum light absorption which occurs near 680 nm. They thus can be excited efficiently by commercially available laser diodes that are compact, reliable and inexpensive and emit light at this wavelength. Suitable commercially available lasers include, for example, Toshiba TOLD9225, TOLD9140 and TOLD9150, Phillips CQL806D, Blue Sky Research PS 015-00 and NEC NDL 3230SU. This near infrared/far red wavelength also is advantageous in that the background fluorescence in this region normally is low in biological systems and high sensitivity can be achieved.

The hydroxyl, carboxyl and isothiocyanate groups of the dyes provide linking groups for attachment to a wide variety of biologically important molecules, including proteins, peptides, enzyme substrates, hormones, antibodies, antigens, haptens, avidin, streptavidin, carbohydrates, oligosaccharides, polysaccharides, nucleic acids, deoxy nucleic acids, fragments of DNA or RNA, cells and synthetic combinations of biological fragments such as peptide nucleic acids (PNAs).

The dyes of this invention have sufficient solubility in aqueous solutions that once they are attached to a soluble biomolecule, the biomolecule retains its solubility. They also have good solubility in organic media, which provides considerable versatility in synthetic approaches to the labeling of desired materials.

Depending upon whether the dye has a reactive carboxyl group, isothiocyanate group or hydroxyl group, the compound is either linked directly to the biomolecule of interest or linked indirectly through phosphoramidite chemistry. The phosphoramidites are useful for labeling such biomolecules as DNA, RNA and peptide nucleic acids. They are useful in dry (i.e., water-free) conditions such as dry acetonitrile. The carboxylic acid reactive groups can react with amine groups of biomolecules in water or aqueous organic solvent mixtures.

When linking a dye carboxylic acid in accordance with this invention to an amine-containing biomolecule, the dye carboxylic acid first is converted to a more reactive form, such as N-hydroxy succinimide (NHS) ester or a mixed anhydride. The amine-containing biomolecule then is treated with the resulting activated acid to form an amide linkage. Typically, this reaction is carried out in mixtures of aqueous buffer and an organic solvent such as DMF at pH 8 to 9.

The attachment of an isothiocyanate dye is analogous to the procedure for the carboxy dye, but no activation step is required. The amine-containing biomolecule is treated directly with the NCS dye to form a thiourea linkage. Typically, the reaction is carried out in mixtures of aqueous buffer and an organic solvent, such as DMF, at pH 8 to 9.

If the dye compound has a reactive hydroxyl group, it is linked to a biomolecule, such as DNA or RNA, through a phosphoramidite chemistry. Use of the phosphoramidite allows labeling of the DNA or RNA during the synthesis process. The protected nucleotide is labeled while attached to a solid phase support. The free 5'—OH group is reacted with the phosphoramidite and a tetrazole activator to form a phosphite linkage which subsequently is oxidized to phosphate. The labeled DNA or RNA then is cleaved from the solid phase using ammonia or other standardized procedure.

As illustrations of the uses of the present invention, the compounds of this invention can be used as labeling reagents for analytical determination of proteins or for automated sequencing of DNA. Standard sequencing methodologies performed with labeled primers can produce high quality sequencing ladders and accurate DNA sequence data.

The compounds of this invention can be attached, for example, to analogs of nucleotide triphosphates (dNTPs and ddNTPs) to provide a reagent for enzymatic labeling of various DNA molecules and for facilitating their detection with an automated DNA sequencing and analysis system. DNA sequencing reaction products can be labeled internally by performing limited polymerization utilizing the labeled dNTP as the sole source of a particular deoxynucleotide prior to a dideoxy-specific termination reaction. PCR products also can be labeled fluorescently by the addition of limited quantities of the labeled dNTP to the amplification reaction. Such labeling can be useful, for example, for the detection of short tandem repeat polymorphisms (STRPs), which in turn are useful for gene mapping, genetic diagnostics, forensic analyses and paternity testing.

Examples of nucleotide analogs and DNA chain terminators that can be labeled with the dyes of this invention include those listed, for example, in U.S. Pat. Nos. 5,332,666; 5,151,507; 5,047,519; 5,091,519; 4,711,955 and 5,241,060 and PCT Application publication WO 9504747. Two specific illustrations of nucleotide triphosphate analogs labeled with a dye of the present invention are represented below:

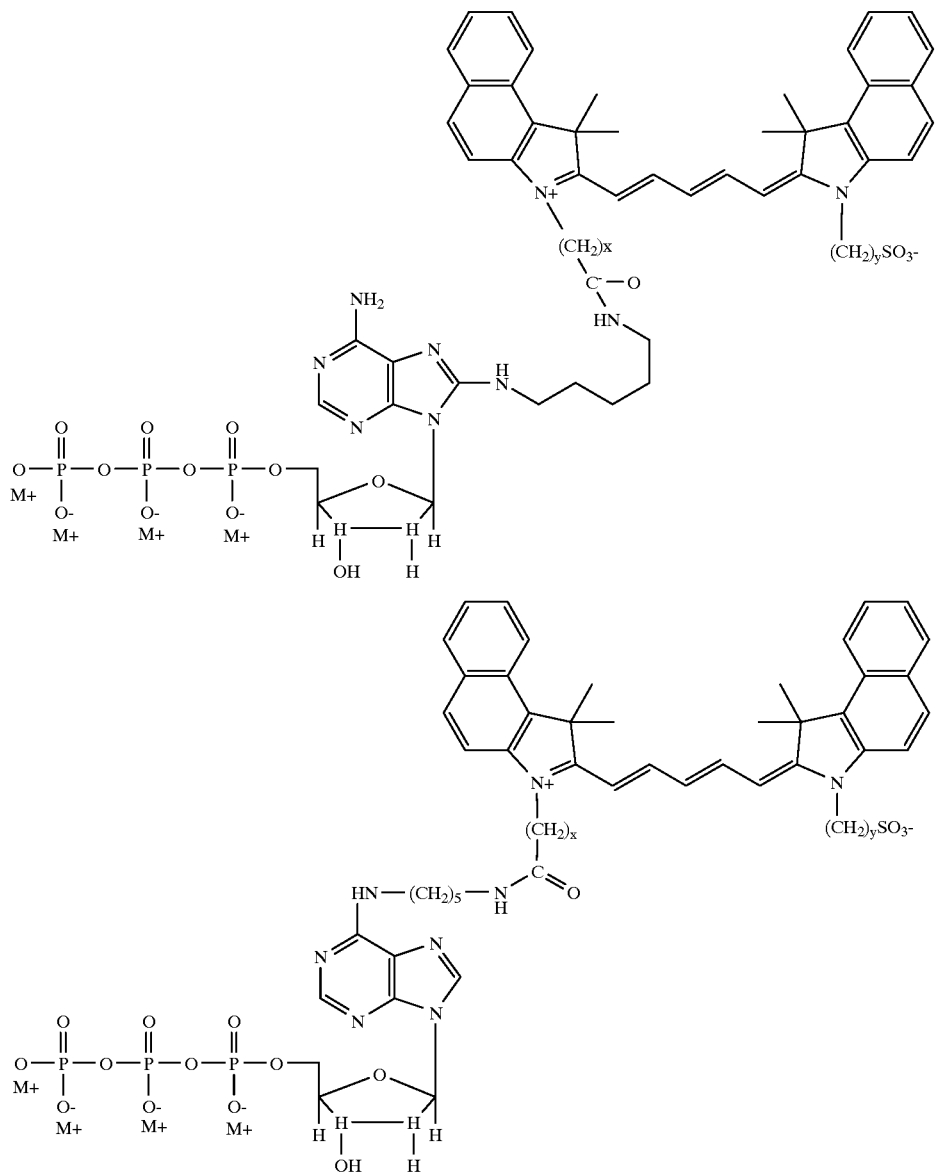

wherein each of x and y, independently, is an integer between 1 and 10 and each M, independently, is selected from Li, Na, K, $NH_4$, $(CH_3)_3NH$, $(CH_3CH_2)_3NH$, $(CH_3CH_2)_4N$ or $(CH_3)_4N$.
Illustrations of terminators to which fluorescent dyes have been attached include:
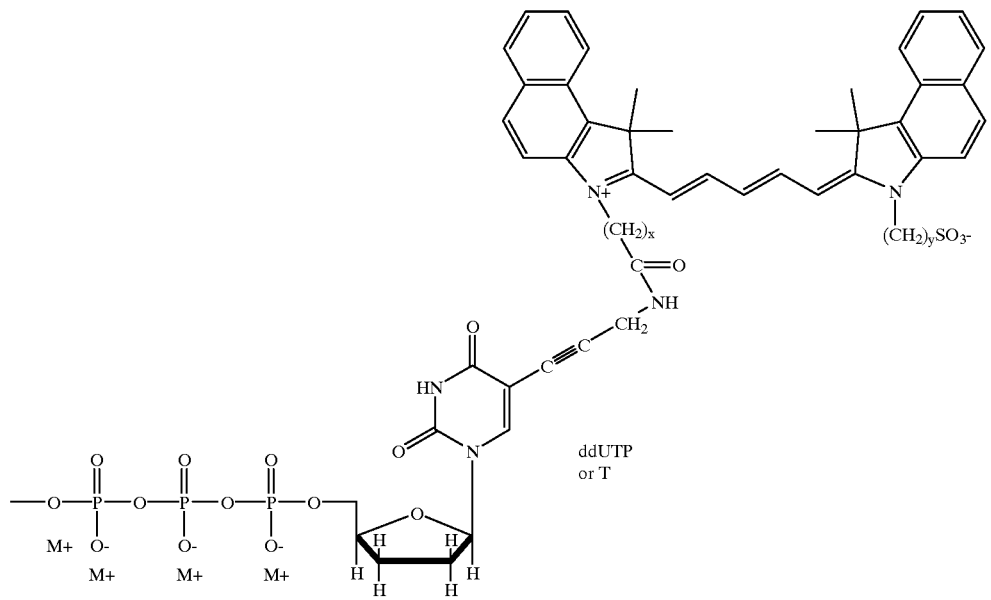
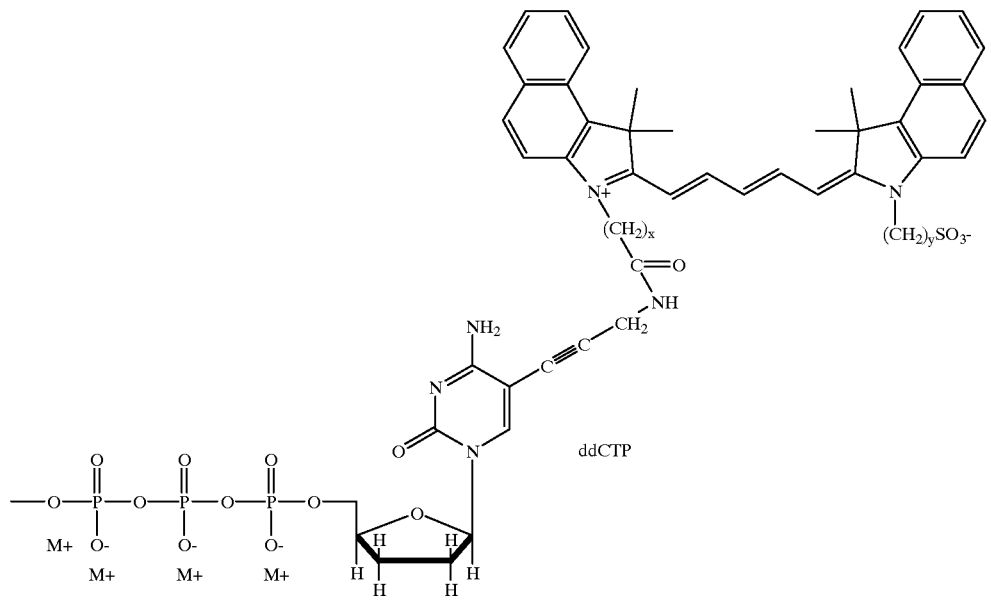

-continued

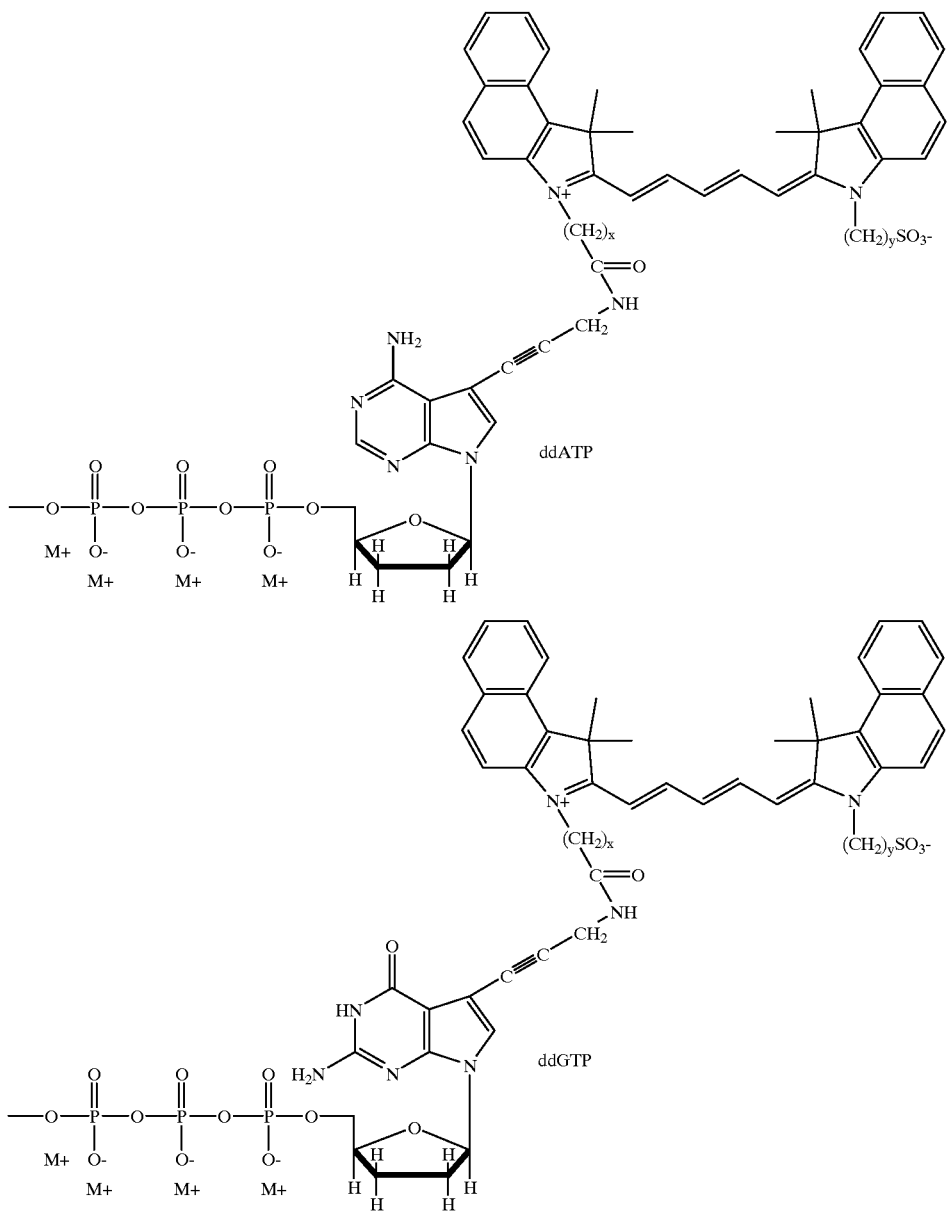

ddATP ddGTP wherein x and y are as defined above.

The fluorescent dye-labeled DNA chain terminators are employed for the generation of fluorescent dye-labeled DNA sequencing fragments. A photometric detection system detects the fragments separated by electrophoresis. Fluorescence detection allows one to either scan a gel containing spatially resolved bands (i.e., resolution in space) or to sit at a single point on the gel and detect bands as they pass sequentially through the detection zone (i.e., resolution in time).

The present invention is illustrated below by the following examples. These examples are provided for illustrative purposes only and are not intended to be construed as limiting the scope of the invention.

EXAMPLE 1

Synthesis of N-(6-hydroxyhexyl)N'-(4-sulfonatobutyl)-3,3,3',3'-tetramethyl benz(e)indodicarbocyanine 9.0 g of 6-bromo-1-hexanol (105 mmol), obtained from Aldrich Chemical Company, Milwaukee, Wis., and 21.96 g. of 1,1,2 trimethyl-1H-benz(e)indole (105 mmol), obtained from ACROS Organics, a division of Fisher Scientific, Pittsburgh, Pa., were heated in a pressure tube with stirring to 95–100° C. The melt solidified after heating for 3 hours. The mixture was heated for an additional 3 hours, cooled and dissolved in 200 ml of chloroform. This solution was extracted three times with 100 ml portions of water. The water layers were combined and extracted three times with 100 ml portions of ether. The aqueous layer was evaporated in vacuo to provide N-(6-hydroxyhexyl)-1,1,2-trimethyl- 1H-benz(e)indolinium bromide in the form of a colorless oil (26.4 g., 65% yield), which could be used without further purification.

390 mg of the N-(6-hydroxyhexyl)-1,1,2-trimethyl-1H-benz(e)indolinium bromide (390 mg, 1 mmol) and N-sulfonatobutyl-1,1,2-trimethyl-1H-benz(e)indole (395 mg, 1 mmol) (obtained in accordance with the procedure taught by Hamer, F. M., in *Cyanine Dyes and Related Compounds*, Weissberger, M. A., ed., Wiley Interscience, N.Y., 1964) were dissolved in pyridine (10 ml) and heated to reflux for 30 minutes, then 250 µl (265 mg, 2.0 mmol) of 1,3,3-trimethoxypropene (also obtained from ACROS Organics) was added dropwise and refluxing was continued for 45 minutes. The resultant mixture was cooled and poured into 100 ml ether and the resulting solid was washed several times with additional 10 ml portions of ether. The crude washed product was recovered after evaporation of the solvent and purified by chromatography on a silica gel column by eluting the column successively with 2 L of 10%, 15% and 20% methanol in chloroform. The yield of the recovered pure hydroxy dye was 97 mg. (14%).

Conversion of the hydroxy dye to the phosphoramidite

The hydroxy dye obtained above (97 mg., 0.140 mmol) was dissolved in 10 ml of dry methylene chloride and stirred under argon at 0° C. for 30 minutes. A solution of bis(N,N-diisopropylamino)-cyanoethyl phosphine (2.13 ml., 0.15 M in methylene chloride) (Monomer Sciences, Huntsville, Ala.) was added to the dye solution. With the solution maintained at 0° C., tetrazole (0.128 ml., 0.5 M) (obtained from PerSeptive Biosystems, Framingham, Mass.) in acetonitrile was added. The cooling was removed after 20 minutes and the reaction was continued for an additional 1.5 hours at room temperature. The reaction mixture was quenched with 5% $NaHCO_3$, washed twice with water and dried with sodium sulfate. The solvent was removed under vacuum and the crude product was taken up in 1.5 ml of methylene chloride. The product was obtained by precipitation into hexane.

Labeled oligonucleotide

The phosphoramidite of the fluorescent dye N-(6-hydroxyhexyl)N'-(4-sulfonatobutyl)-3,3,3',3'-tetramethyl-benz(e)indodicarbocyanine can be used to label DNA molecules prepared in a DNA synthesis machine. The dye is attached to the 5' end of the protected, support-bonded oligonucleotide via standard phosphoramidite chemistry. On syntheses at 200 nmol scale typical crude yields of dye-labeled oligonucleotides are 150 nmol or higher.

Each of the DNA oligonucleotides M13 fwd (-29), M13 rev, T7, T3 and SP6, was synthesized in the PerSeptive Biosystems Expedite 8909 DNA synthesis machine in accordance with standard reagents and the methodology taught by the manufacturer. The same apparatus then was used to attach the fluorescent label to the 5' end of each oligonucleotide by treatment with a 0.1M solution of the dye phosphoramidite produced above in acetonitrile. For the attachment of the dye phosphoramidite a three minute delay was inserted after the delivery of the dye in the tetrazole to the synthesis column to allow additional time for the coupling reaction. The 5'-fluorescent labeled DNA oligonucleotide was produced following oxidation, cleavage, deprotection and purification by HPLC. For HPLC purification of the labeled oligonucleotide, a C18 reverse phase column having 5µ particles, 300 A pore size (Waters DeltaPak), 1.7 ml/min was used. Solvent A was 4% acetonitrile in 0.1M triethylammonium acetate and Solvent B was an 80% acetonitrile in 0.1M triethylammonium acetate. The gradient profile was 10 to 45% B over 35 minutes, 45 to 100% B over 15 minutes, 100 to 10% B in 10 minutes. The labeled oligonucleotide eluted at about 40 minutes.

The labeled oligonucleotide can be used, for example, as a primer in the Sanger method of DNA sequencing referenced above, as a tailed primer for genotyping or as a hybridization probe.

EXAMPLE 2

Synthesis of N-(5-carboxypentyl)N'-(4-sulfonatobutyl) 3,3,3', 3'-tetramethylbenz(e) indodicarbocyanine N-(5-carboxypentyl)-1,1,2-trimethyl-1H-benz(e) indolinium bromide (100 mg., 0.25 mmol) (made in accordance with the procedure taught by Hamer, F. M. in *Cyanine Dyes and Related Compounds*, Weissberger, M. A., ed., Wiley Interscience, N.Y., 1964) and N-sulfonatobutyl-1,1, 2-trimethyl-1H-benz(e)indole (85 mg., 0.25 mmol) (also in accordance with the procedures in *Cyanine Dyes and Related Compounds*, supra) were dissolved in 10 ml. pyridine and heated to reflux for 1 hour. Subsequently, 1,3,3-trimethoxypropene (66 mg., 0.50 mmol) (obtained from ACROS Organics) was added dropwise to the refluxing solution and heating was continued for 2 hours. The solvent was removed under vacuum and the residue was purified by chromatography on a silica gel column using a methylene chloride and methylene chloride/methanol gradient as in Example 1. The yield was 89 mg (0.126 mmol., 50%) of the desired dye carboxylic acid.

Labeling nucleotides with the dye carboxylic acid

The dye carboxylic acid (5 mg., 0.007 mmol) was dissolved in dry DMF and treated with N,N-diisopropylethylamine (DIPEA) (2.75 mg., 0.021 mmol) and then with ethyl chloroformate (1.5 mg, 0.014 mmol) and stirred at room temperature for four hours. The reaction solvent, DIPEA, and ethyl chloroformate were removed under vacuum. The resulting mixed anhydride was used without any further treatment or purification in the following step.

A nucleotide triphosphate, 8-(5-aminopentylamino)-2'-deoxyadenosine-5'-triphosphate (from Boehringer Mannheim Biochemicals) (4.5 mg, 0.0073 mmol, 1.04 eq.) was dissolved in borate buffer at pH 8.5 and the mixed anhydride from the foregoing reaction (0.007 mmol) in DMF (both equal volumes) were mixed together and the reaction followed by HPLC. The labeled nucleotide conjugate was purified by preparative HPLC.

The same procedure was followed using N6-deaza dATP as the nucleotide triphosphate (obtained from DuPont NEN).

The labeled oligonucleotide can be used, for example, in genotyping or Cycle Labeling and Sequencing (CLS).

EXAMPLE 3

Alternate Synthesis Route

N-4-sulfonatobutyl-1,1,2-trimethyl-1H-benz(e)indole (690 mg., 2.0 mmol), synthesized in accordance with the procedure set forth in *Cyanine dyes and Related Compounds*, referenced above, and malonaldehyde bis (phenylimine)monohydrochloride (518 mg, 2.0 mmol) obtained from Aldrich Chemical Co. (catalog #38353-8) were dissolved in 50 ml of acetic anhydride and the mixture heated to 125° C. over an oil bath for 30 minutes. The acetic anhydride was removed under high vacuum and washed with ether (3×100 ml). the residual brown solid obtained was dried (900 mg, 93%) and used without further purification for the synthesis of a desired dye.

To make the dye of Example 1, 276 mg. (0.57 mmol) of the salt adduct obtained from the foregoing procedure was mixed with N-(6-hydroxy hexyl) 1,1,2-trimethyl-1H-benz (e)indoleninium bromide (224 mg., 0.57 mmol) in a flask and the solids were dissolved in pyridine (15 ml). the mixture was heated to 125 ° C. for 30 minutes. The pyridine was removed under vacuum. The asymmetric dye formed was the only dye product by TLC. Crude yield was about 400 mg. Purification using silica gel column chromatography is expected to give >90% yield.

To make the dye of Example 2, the same procedures were followed, mixing 100 mg (0.208 mmol) of the salt adduct with 84 mg (0.208 mmol) N-(carboxy pentyl)-1,1,2-trimethyl-1H-benz(e)indoleninium bromide in 10 ml of pyridine. The crude yield of the desired product was approximately 150 mg. Purification using silica gel chromatography is expected to give >90% yield.

EXAMPLE 4

Labeled Primer

The M13 fwd (-29) primer (1.5 pmol) labeled with the cyanine dye via the phosphoramidite in Example 1 was used to sequence M13 vector (purchased from Epicentre Technologies Corporation, Madison, Wis.) (0.2 pmol) in accordance with the SequiTherm™ Cycle Sequencing Protocol (Sequencing Bulletin #13 published by LI-COR, Inc., Lincoln, Neb.). In brief, the procedures were as follows:

The following were combined in a 0.5 ml microcentrifuge tube:

M13 vector: 0.2 pmol 680 nm dye-labeled M13 fwd (-29) primer: 1.5 pmol

10× sequencing buffer

SequiTherm™ thermostable DNA polymerase ddH$_2$O to bring total volume to 17 µl.

Four 0.2 ml thermocycler tubes were labeled A,T,G and C. Into each tube was placed 2.0 µl of the appropriate SequiTherm™ Long-Read Termination mix. 4.0 µl of the template/primer/enzyme mix from the microcentrifuge tube above were pipetted into each of the four thermocycler termination tubes.

A drop (10–15 µl) of mineral oil was placed on top of the reaction mixture in each of the four thermocycler tubes. The four tubes were inserted in the thermocycler and the thermocycler was started. The thermocycler was programmed for the following cycles:

a. 95° C. for 2 minutes b. 95° C. for 30 seconds c. 60° C. for 15 seconds d. 70° C. for 15 seconds steps b–d were repeated for a total of 30 cycles e. 4° C. soak After the cycling was completed, 4.0 µl of SequiTherm™ Stop Solution was injected into each of he reaction mixtures under the mineral oil and mixed thoroughly. The samples were denatured by heating at 95° C. for three minutes.

The resulting array of labeled DNA fragments was loaded onto a 41 cm electrophoresis gel (6% deionized LongRanger™ solution) in a LI-COR Model 4200 Automated DNA Sequencer. The solution was made as follows: 25.2 g urea were added to 7.2 ml of LongRanger™ 50% gel concentrate (FMC Bioproducts Rockland, Me.) and the volume was brought up to 52.8 ml with ddH$_2$O. 7.2 ml of standard 10× TBE buffer was added and the solution was mixed. The gel solution was added to a filter cup and filtered.

Electric current was applied. The electrophoresis parameters were those set forth in Sequencing Bulletin #28 published by LI-COR, Inc.:

| Parameter | 41 cm Apparatus |
| --- | --- |
| Gel thickness | 0.25 mm |
| Gel composition | 5% Long Ranger ™ |
| Buffer type | 10× TBE (890 mM TRIS, 890 mM Boric Acid, 20 mM EDTA) |
| Gel buffer | 1.2× TBE |
| Running buffer | 1.0× TBE |
| Voltage | 1500 V |
| Current | 35.0 mA |
| Power | 31.5 W |
| Temperature | 50° C. |
| Pre-run time | 30 minutes |
| Total run time | 7 hours |

As the fragments passed the detector at the other end of the gel, fluorescence was excited with a 680 nm laser diode and detected from 710 to 750 nm. A high quality sequence ladder was obtained.

EXAMPLE 5

Labeled dATP Analogs (Internal Labels)

N6-deaza dATP labeled with N-(5-carboxypentyl) N'-(4-sulfonatobutyl)-3,3,3', 3'-tetramethyl-benz(e) indodicarbocyanine (10 pmol), made in accordance with the procedures in example 2, was used with unlabeled M13 fwd (-29) primer (4 pmol) to sequence M13 vector (0.3 pmol) (obtained from Epicentre Technologies Corporation, Madison, Wis.). The Cycle Labeling and Sequencing (CLS) method for sequencing DNA is a two step procedure which involves cycle labeling where an unlabeled primer is partially extended and labeled with three dNTPs and infrared dye-labeled dATP and cycle sequencing where the labeled primer is used in dideoxy chain termination reactions. The procedure was done in accordance with the teachings of Sequencing Bulletin #41 published by LI-COR, Inc. The procedure briefly was as follows:

The following reagents were combined in a 0.2 ml PCR tube:

M13 vector: 0.3 pmol primer: 4 pmol dNTP Mix (5 µM of dCTP, dGTP and dTTP)

dye-labeled N6-deaza dATP:10 pmol

10× SequiTherm reaction buffer

SequiTherm™ DNA polymerase: 5U/µl sterile, deionized water to bring total volume to 17 µl The reagents were mixed well, a drop of mineral oil was placed on top of the reaction mixture and the tube was inserted in an MJ Research thermal cycler. The following labeling reaction program for the thermocycler was set:

a. 92° C. for 2 minutes b. 92° C. for 30 seconds c. 40° C. for 10 seconds d. 50° C. for 15 seconds e. 70° C. for 15 seconds repeat steps b to e for a total of 30 cycles f. 4° C. soak Four 0.2 ml PCR tubes were labeled A, T, G and C. Two μl of the appropriate LongRead™-LC termination mix was added to each tube. Four μl from the above labeling reaction (4.2 μl setting on a P20 Gilson® Pipetman® to account for mineral oil) were added to each termination mixture. The contents were mixed well and a drop of mineral oil was placed on each reaction mixture. The tubes were placed in the thermal cycler and the cycle sequencing reaction program was used. When the cycle sequencing was completed, each reaction mixture was pipetted from under the mineral oil into a 0.5 ml tube. The samples were denatured at 95° C. for 2 minutes, chilled on ice and 2.0 μl of each sample were loaded onto an electrophoresis gel in a LI-COR Model 4200 Automated DNA Sequencer and an electric current was applied in accordance with the conditions set forth in Example 4 above. As the fragments passed the detector at the other end of the gel, fluorescence was excited with a 680 nm laser diode and detected from 710 to 750 nm.

What is claimed is:

1. A fluorescent dye having the general formula:

FORMULA 1

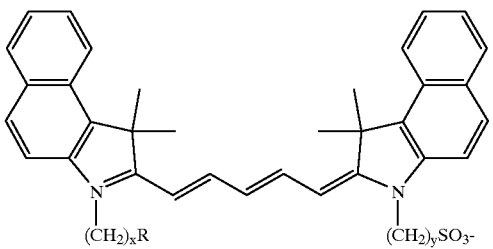

wherein R is —NCS, and x and y, independently, are integers between 1 and about 10.

2. A dye-labeled nucleotide analog comprising the general structure

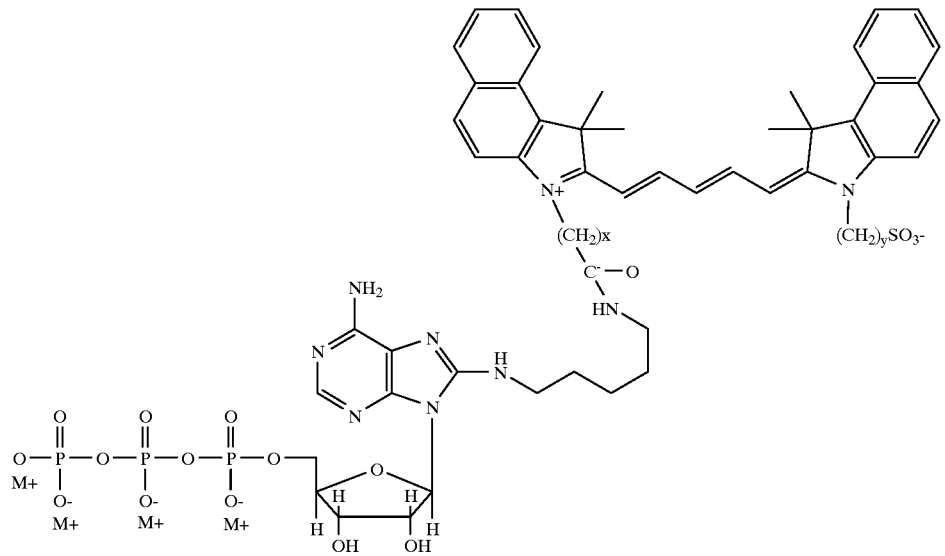

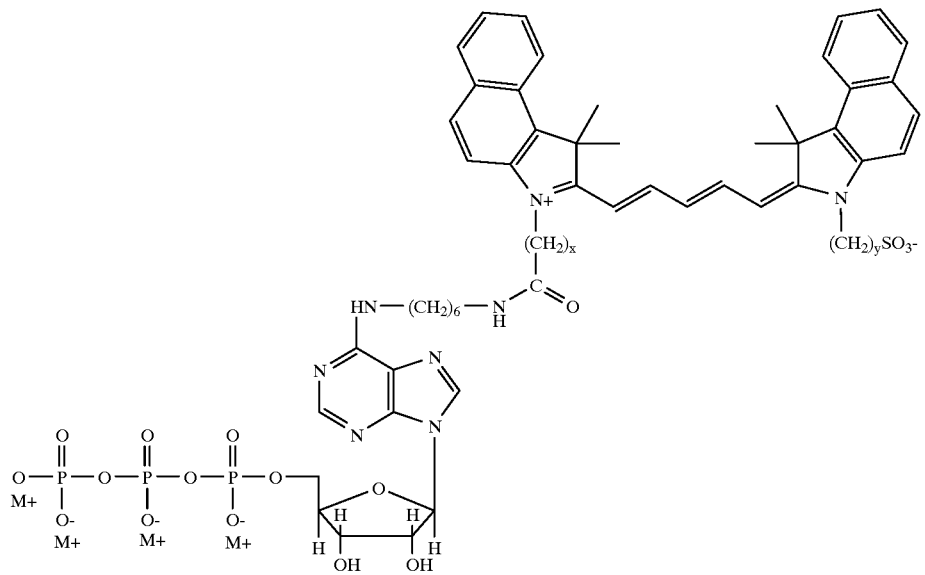

wherein each of x and y, independently, is an integer between 1 and 10 and each M, independently, is selected from Li, Na, K, $NH_4$, $(CH_3)_3NH$, $(CH_3CH_2)_3NH$, $(CH_3CH_2)_4N$ or $(CH_3)_4N$.

4. A dye-labeled nucleotide analog in accordance with claim 2 or 3, wherein each of x and y is an integer from 2 to 6.

5. A fluorescent dye labeled DNA chain terminator having the general structure:

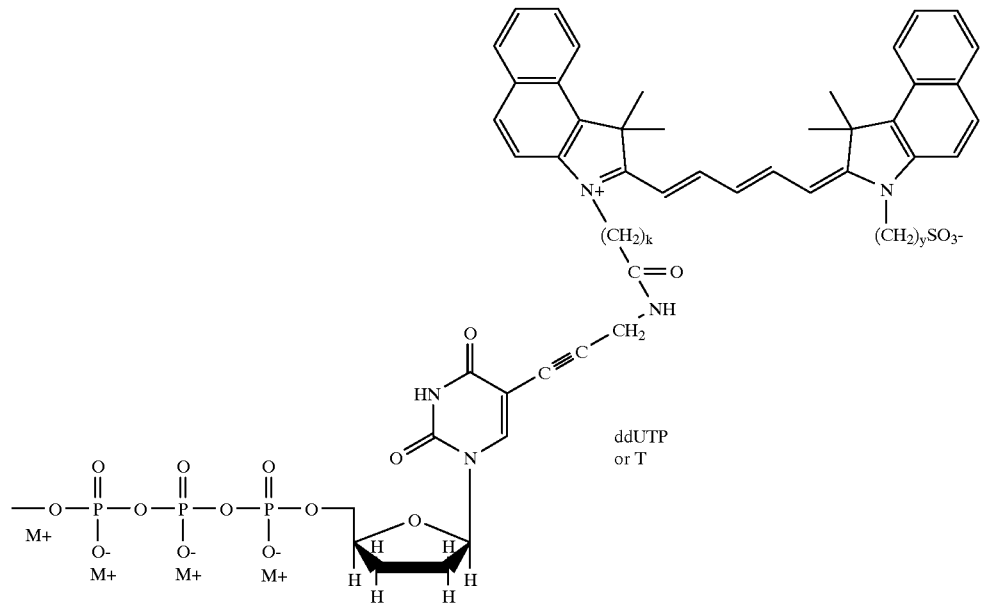

wherein each of x and y, independently, is an integer selected from 1 to about 10.

6. A fluorescent dye labeled DNA chain terminator having the general structure:

wherein each of x and y, independently, is an integer selected from 1 to about 10.

7. A fluorescent dye labeled DNA chain terminator having the general structure:

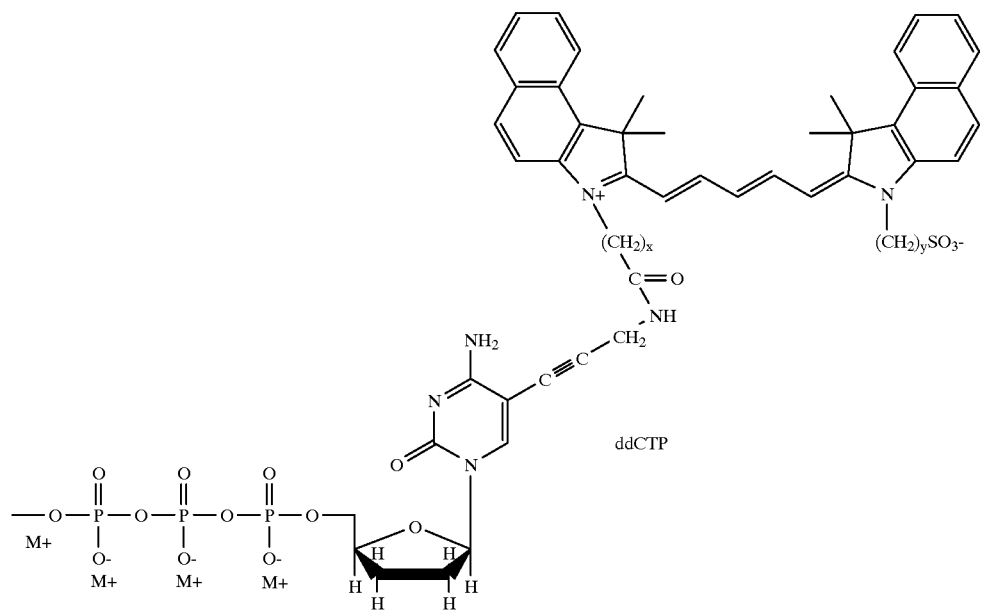

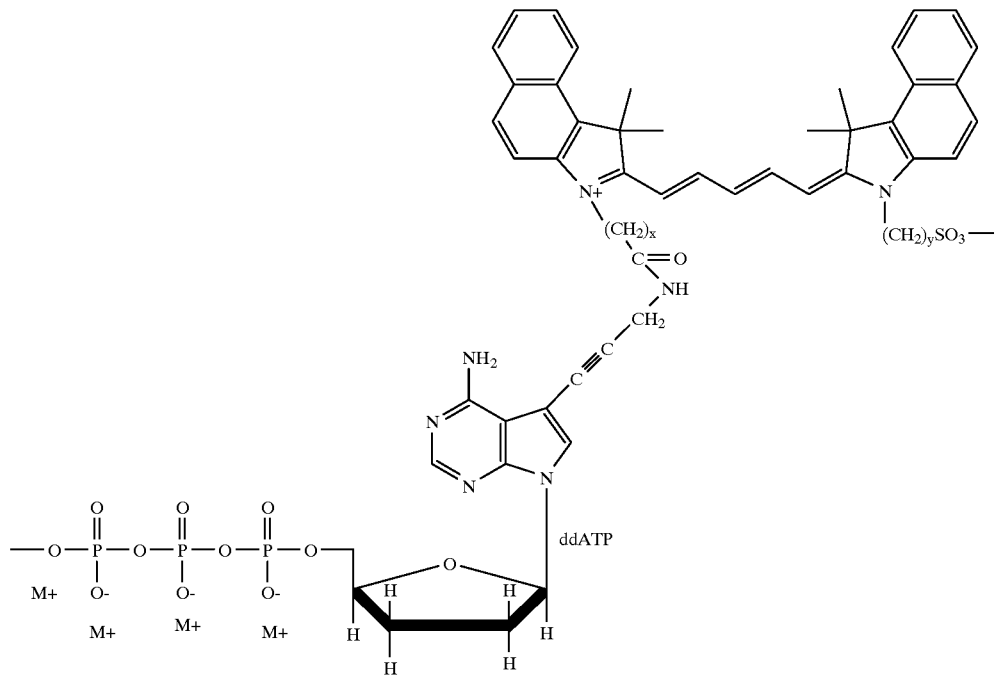

wherein each of x and y, independently, is an integer selected from 1 to about 10.

8. A fluorescent dye labeled DNA chain terminator having the general structure:

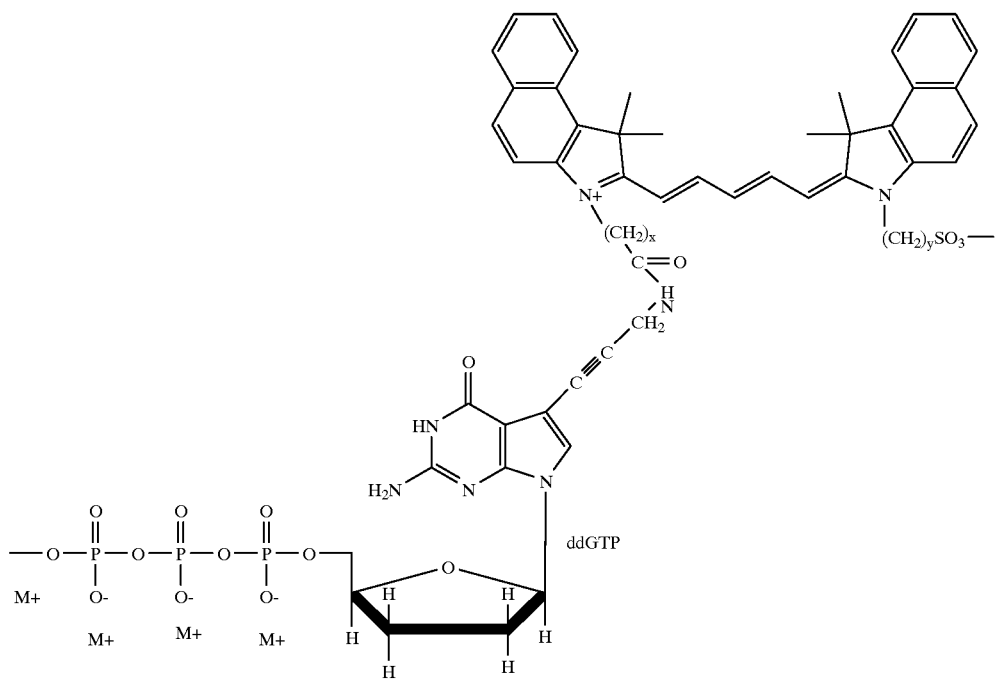

wherein each of x and y, independently, is an integer selected from 1 to about 10.

9. A fluorescent dye-labeled DNA chain terminator in accordance with claim 5, 6, 7 or 8 where each of x and y independently is an integer from 2 to 6.

10. N-(6-hydroxyhexyl)-1,1,2-trimethyl-1H-benz(e)indolinium halide.

11. N-(6-hydroxyhexyl)-1,1,2-trimethyl-1H-benz(e)indolinium bromide.

12. A phosphoramidite derivative of a dye having the general formula

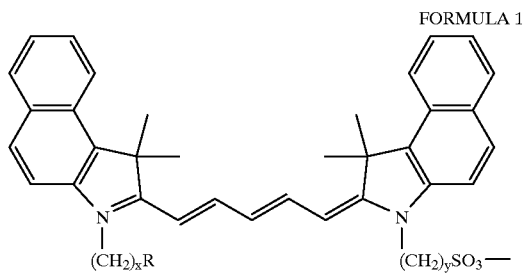

FORMULA 1 wherein R is —O—phosphoramidite and x and y, independently, are integers between 1 and about 10.

13. A nucleotide analog labelled with a dye of the general formula:

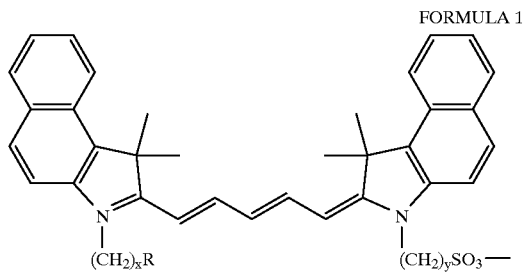

FORMULA 1 wherein R is —OH, —CO$_2$H, NH$_2$ or —NCS, and x and y, independently, are integers between 1 and about 10.

14. A DNA chain terminator labelled with a dye of the general formula:

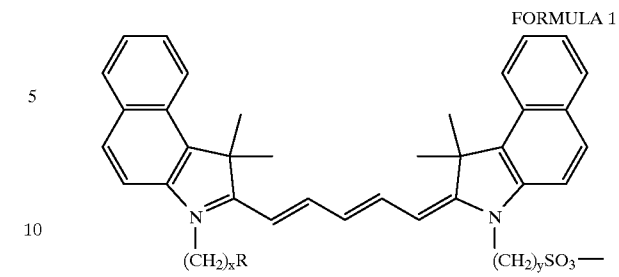

FORMULA 1 wherein R is —OH, —CO$_2$H, —NH$_2$ or —NCS and x and y, independently, are integers between 1 and about 10.

15. A dye phosphoramidite having the formula.

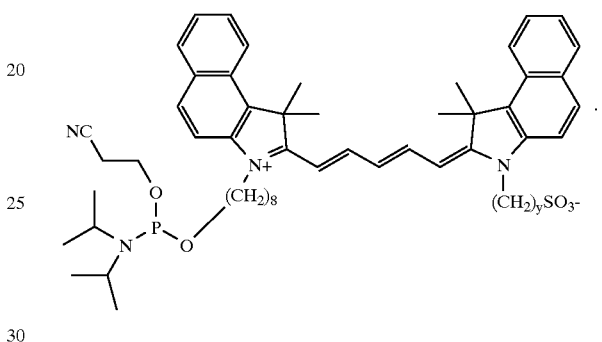

16. An oligonucleotide labeled with a dye phosphoramidite of claim 12.

17. An oligonucleotide labeled with a dye phosphoramidite of claim 15.

* * * * *